United States Patent [19]

Peglion et al.

[11] Patent Number: 5,296,482
[45] Date of Patent: Mar. 22, 1994

[54] (BENZOCYCLOALKYL) ALKYLAMINES

[75] Inventors: Jean-Louis Peglion, Le Vesinet; Joel Vian, Chaville; Jean-Paul Vilaine, Chatenay Malabry; Nicole Villeneuve, Rueil Malmaison; Philip Janiak, Clichy; Jean-Pierre Bidouard, Chilly Mazarin, all of France

[73] Assignee: Adir et Compagnie, Courbevoie, France

[21] Appl. No.: 950,957

[22] Filed: Sep. 25, 1992

[30] Foreign Application Priority Data

Sep. 27, 1991 [FR] France ................. 91 11894

[51] Int. Cl.⁵ ............... A61K 31/55; C07D 223/16
[52] U.S. Cl. ..................... 514/213; 514/217; 540/522; 540/523
[58] Field of Search .......... 540/533, 523, 522; 514/213, 217

[56] References Cited

U.S. PATENT DOCUMENTS 4,542,153  9/1985  Witiak et al. .................. 514/466

FOREIGN PATENT DOCUMENTS 0161604 11/1985 European Pat. Off. ........... 540/523

OTHER PUBLICATIONS

J. D. McDermed et al., J. Med. Chem. 1975, 18(4), 362-367: "Synthesis and Pharmacology of some 2-Aminotetralines. Dopamine receptor agonists".

A. M. Johansson et al., Molecular Pharmacology, 1986, 30, 258-269: "2-aminotetralins: affinities for dopamine $D_2$ receptors, molecular structures and conformational preferences".

Anders Karlent et al., J. Med. Chem., 1989, 32, 765-774: "Topography and conformational preferences of 6,7,8,9-tetrahydro-1-hydroxy-N,N-dipropy-5H-benzocyclohepten-6-ylamine. A rationale for the dopaminergic inactivity".

J. G. Cannon et al., J. Med. Chem., 1984, 27, 922-923: "Catechol Derivatives of 6-Aminobenzocycloheptene: Assessment of Dopaminergic Effects".

J. G. Cannon et al., J. Med. Chem. 1972, 15(4), 348-350: "Centrally Acting Emetics. 6. Derivatives of beta-- Naphthylamine and 2-Indanamine".

Michele Bernier, et al., Am. J. Physiol., 1989 256, H21-H31: "Ischemia-induced and reperfusion-induced arrhythmias: importance of heart rate".

Primary Examiner—Mark L. Berch
Assistant Examiner—P. K. Sripada
Attorney, Agent, or Firm—Gordon W. Hueschen

[57] ABSTRACT

The compounds are 3-[(benzocycloalkyl)alkyl amino alkyl]-1,3,4,5-tétrahydro 2H-3-benzazepin-2 ones useful in cardiovascular field.

A compound disclosed in (R,S)-7,8-dimethoxy-3-{3-{N-[4,5-dimethoxybenzocyclobut-1-yl) methyl]-N-methyl amino}propyl}-1,3,4,5-tetrahydro-2H-3-benzazepin-2-one.

9 Claims, No Drawings

(BENZOCYCLOALKYL) ALKYLAMINES

The present invention relates to new (benzocycloalkyl)alkylamines, a process for their preparation and pharmaceutical compositions containing them.

It relates more especially to compounds of formula (I):

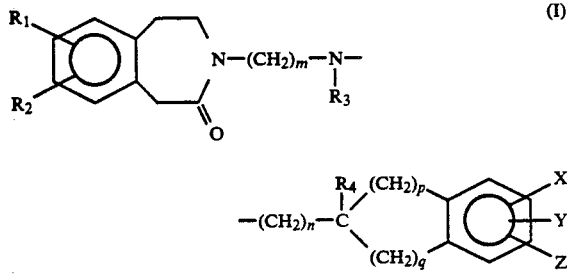

in which
- m represents an integer from 2 to 5 inclusive,
- n represents an integer from 1 to 6 inclusive,
- p and q, which are the same or different, each represents 0 or an integer 1 or 2,
  with the proviso that the sum of p and q is equal to 1 or 2,
- $R_1$ and $R_2$, which are the same or different, each represents a group selected from:
  hydrogen,
  halogen,
  hydroxy,
  lower alkoxy,
  phenyl-lower alkoxy,
  and substituted phenyl-lower alkoxy,
  or $R_1$ and $R_2$, when they are carried by 2 adjacent carbon atoms, together form an —O—(CH$_2$)$_r$—O— group in which r represents an integer 1 or 2,
- $R_3$ represents a group selected from;
  hydrogen,
  lower alkyl,
  lower alkenyl,
  cycloalkyl,
  cycloalkyl-lower alkyl,
  phenyl-lower alkyl,
  substituted phenyl-lower alkyl,
  —CO—$R_5$ or —CO—O—$R_5$
  $R_5$ representing a group selected from: hydrogen, lower alkyl, lower alkenyl, lower alkynyl, phenyl, substituted phenyl, phenyl-lower alkyl, substituted phenyl-lower alkyl, cyclo-lower alkyl, and cycloalkyl-lower alkyl,
  and —CO—NR$_6$R$_7$ wherein $R_6$ and $R_7$ are the same or different and each has the same meanings as those of the group $R_5$ as defined above,
  or $R_6$ or $R_7$, with the nitrogen atom carrying them, together form a saturated ring having from 4 to 7 chain members,
- $R_4$ represents a hydrogen atom or a lower alkyl radical;
- X, Y and Z, which are the same or different, each represents a group selected from:
  hydrogen,
  halogen,
  hydroxy,
  lower alkoxy,
  and substituted phenyl-lower alkoxy,
  or X and Y, or Y and Z, when they are carried by 2 adjacent carbon atoms, together from an —O—(CH$_2$)$_r$—O— group in which r represents an integer 1 or 2, an —O—(CH$_2$)$_2$— group or an —O—CH=CH— group;

the term "substituted" describing the groups "phenyl", "phenyl-lower alkyl" and "phenyl-lower alkoxy" indicating that those groups may be substituted in the phenyl nucleus by one or more substituents selected from halogen atoms and the radicals hydroxy, trifluoromethyl, lower alkyl and lower alkoxy, the terms "lower alkyl" and "lower alkoxy" indicating saturated linear or branched groups containing from 1 to 6 carbon atoms inclusive, the terms "lower alkenyl" and "lower alkynyl" indicating unsaturated linear or branched groups containing from 2 to 6 carbon atoms inclusive, the term "cycloalkyl" indicating a saturated hydrocarbon ring containing from 3 to 8 chain members, their possible optical isomers, isolated or in the form of a mixture, as well as, where applicable, their addition salts with a pharmaceutically acceptable acid.

The closest prior art is illustrated especially by 3-benzazepin-2-one compounds substituted by phenylalkylamine groups of formula (a):

in the Application EP 0 065 229, or substituted by aminated 1,2,3,4-tetrahydronaphthalene groups of formula (b):

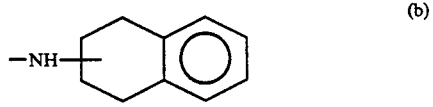

in the Application EP 0 161 604. These prior art compounds are presented in the 2 applications as bradycardic agents.

The compounds of the present invention are distinguished from those of the prior art by the presence, in place of the groups (a) and (b) defined above, of (benzocyclobut-1-yl)alkylamine and (indan-2-yl)alkylamine groups. The discovery by the Applicant not only of powerful bradycardic but also of anti-arrhythmic and anti-ischaemic activities, having a long duration of action, is therefore surprising since such (benzocyclobut-1-yl)alkylamine and (indan-2-yl)alkylamine groups replace, very advantageously, the groups of formula (a) and (b) of the prior art.

Those differences in structure furthermore result in compounds that are distinguished from those of the prior art by an improved selectivity and a longer duration of action.

The invention extends also to a process for the preparation of compounds of formula (I) which is characterised in that: an amine of formula (II):

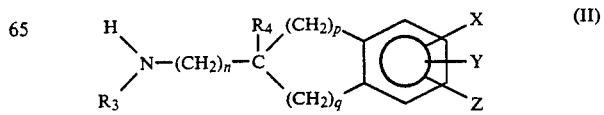

in which $R_3$, $R_4$, X, Y, Z, n, p and q are as defined for formula (I), in racemic or optically active form when there is an asymmetric carbon atom present, is condensed with a compound of formula (III):

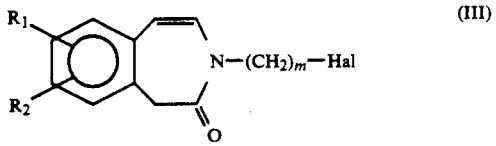

in which $R_1$, $R_2$ and m are as defined for formula (I) and Hal represents a halogen atom, to yield a compound of formula (IV):

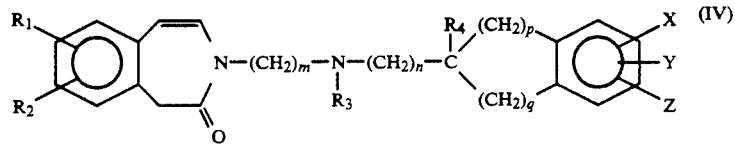

in which $R_1$, $R_2$, $R_3$, $R_4$, X, Y, Z, m, n, p and g are as defined hereinbefore, in racemic or optically active form when an asymmetric carbon atom is present, which compound of formula IV is subjected to hydrogenation to yield a compound of formula (I):

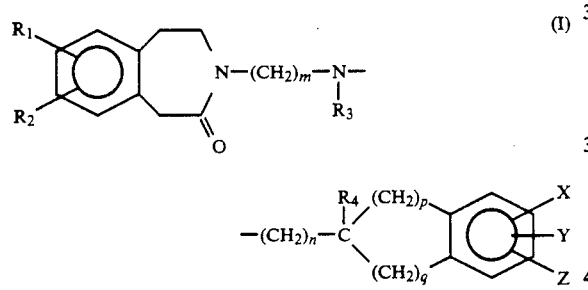

in which $R_1$, $R_2$, $R_3$, $R_4$, X, Y, Z, M, n, p and q are as defined hereinbefore, in racemic or optically active form when there is an asymmetric carbon atom present, which compound of formula (I) is, if desired:

purified by a conventional method of crystallisation and/or chromatography, and/or converted into a salt with a pharmaceutically acceptable acid, it being understood that the compounds of formula (I), when they contain an asymmetric carbon atom, may be prepared in an optically active form, not only by using optically active starting materials but also starting from corresponding racemic compounds of formula (I), by using conventional methods of separation of optical isomers.

The compounds of formula (IV) are new and form part of the invention in the same way as the compounds of formula (I) for which they constitute intermediates in the preparation process.

The compounds of formula (I) may be converted into addition salts with acids, which salts, as such, form part of the invention. There may be mentioned as acids for the formation of those salts, for example, in the mineral series hydrochloric, hydrobromic, sulphuric, nitric and phosphoric acid, and in the organic series acetic, propionic, maleic, fumaric, tartaric, oxalic, benzoic, methanesulphonic, isethionic, benzenesulphonic . . . acids.

The pharmacological properties of the compounds of the present invention reveal their therapeutic value in the cardiovascular field.

Studies carried out in vivo exhibit their powerful specific activity having a long duration of action, reducing cardiac frequency and bringing about a reduction in the myocardial consumption of oxygen.

The studies carried out confirm that the activity of those compounds is directly on the sino-auricular node and is distinguished from that of 3-adrenergic receptor antagonists and of calcium channel inhibitors especially by the absence of depressive effects on auriculo-ventricular conduction and on cardiac contractile function.

Those properties permit the use of compounds of the invention as curative or preventative medicaments of various clinical conditions of myocardial ischaemia resulting from an imbalance between the supply and demand of myocardial oxygen, such as angina of the chest, myocardial infarction and associated rhythm disorders, as well as various pathologies involving rhythm disorders, especially supra-ventricular rhythm disorders.

Those compounds can also reduce the complications of atherosclerotic, especially coronary, lesions by limiting vascular haemodynamic constraints.

The present invention also relates to pharmaceutical compositions comprising a compound of the formula I or an addition salt thereof with a pharmaceutically acceptable acid, alone or in combination with one or more inert, non-toxic, pharmaceutically acceptable carriers or excipients.

The so-obtained pharmaceutical compositions are generally presented in dosage form. They may, for example, be in the form of tablets, dragées, capsules, suppositories or injectable or drinkable solutions, and may be administered by the oral, rectal, intramuscular or parenteral route.

The dosage may vary, especially in accordance with the age and weight of the patient, the route of administration, the nature of the disorder and associated treatments, and comprises the administration of from 1 to 100 mg from one to several times per day.

The following Examples illustrate the invention without implying any limitation.

The melting points are determined using a Kofler hot plate. The 1H nuclear magnetic resonance spectra (NMR) are carried out using tetramethylsilane (TMS) as internal reference. The chemical shifts are expressed in parts per million (ppm).

The starting materials used in the following Examples are either known products, or products prepared from known substances in accordance with processes described for the preparation of analogous products.

EXAMPLE 1

(R,S)-7,8-dimethoxy-3-{3-{N-[(4,5-dimethoxybenzocyclobut-1-yl)methyl]-N-(methyl)amino)propyl)-1,3,4,5-tetrahydro-2H-3-benzazepin-2-one

STEP A:
(R,S)-N-[(4,5-dimethoxybenzocyclobut-1-yl)-methyl]-N-(methyl)amine

STAGE A₁:
(R,S)-N-[(4,5-dimethoxybenzocyclobut-1-yl)methyl]amine hydrochloride 312 cm³ of a molar solution of borane complexed with tetrahydrofuran are added dropwise at room temperature, with stirring, to a solution of 25 g of (R,S)-1-(cyano)-4,5-(dimethoxy)-benzocyclobutane in 250 cm³ of tetrahydrofuran. The reactants are left in contact for 12 hours, then 200 cm³ of ethanol are added and the whole is stirred for 1 hour. 100 cm³ of 3.3N ethereal hydrogen chloride are added dropwise. 27.7 g of the desired compound are obtained.

Yield: 90%
Melting point 205° C.

STAGE A₂:
(R,S)-N-[(4,5-dimethoxybenzocyclobut-1-yl)methyl]-N-(ethoxycarbonyl)amine 1.5 cm³ of ethyl chloroformate are poured onto a suspension consisting of 3.4 g of the compound obtained in Stage A₁, 4.5 cm³ of triethylamine and 50 cm³ of dichloromethane. The whole is stirred for one night at room temperature and then washed with water and with 1N hydrochloric acid and dried. The solvent is evaporated to dryness, yielding 3.2 g of an oil which corresponds to the desired compound.

Yield: 80%

STAGE A₃:
(R,S)-N-[(4,5-dimethoxybenzocyclobut-1-yl)methyl]-N-(methyl)amine 3.2 g of the compound obtained in Stage A₂ dissolved in 30 cm³ of tetrahydrofuran are added to a suspension of 0.9 g of lithium aluminum hydride in 20 cm³ of tetrahydrofuran. The whole is refluxed for 1½ hours and subsequently hydrolysed with 0.6 cm³ of water, then with 0.5 cm³ of 20% sodium hydroxide solution and finally with 2.3 cm³ of water. The mineral salts are then filtered off and rinsed with tetrahydrofuran and the filtrate obtained is evaporated to dryness. 2.3 g of the compound of Step A are obtained.

Yield: 92%

STEP B:
7,8-dimethoxy-3-[3-iodopropyl]-1,3-dihydro-2H-3-benzazepin-2-one

A suspension of 12 g of 7,8-dimethoxy-3-[3-chloropropyl]-1,3-dihydro-2H-3-benzazepin-2-one obtained in accordance with the method described in the literature (Reiffer M. et al., J. Med. Chem. 1990; vol 33 (5): 1496-1504) and 6.2 g of sodium iodide in 50 cm³ of acetone are refluxed for 24 hours. After filtration and evaporation to dryness of the solvent, the residue is taken up in water and extracted with dichloromethane. The extract is separated off, dried over anhydrous magnesium sulphate and then concentrated in vacuo to yield 15.2 g of the desired compound.

Yield: 99%

Melting point 132°-134° C.

Spectral characteristics: NMR (CDCl₃) 6.8 ppm, 2 singlets, 2H; 6.35-6.2 ppm, 2 doublets, 2H; 3.9 ppm, 2 singlets, 6H; 3.6 ppm, triplet, 2H; 3.45 ppm, multiplet, 2H; 3.1 ppm, triplet, 2H; 2.1 ppm, multiplet, 2H.

STEP C:
(R,S)-7,8-dimethoxy-3-{3-{N-[(4,5-dimethoxybenzocyclobut-1-yl)methyl]-N-(methyl)amino)propyl)-1,3-dihydro-2H-3-benzazepin-2-one A mixture composed of 5.6 g of potassium carbonate, 2.2 g of the compound obtained in Step A in 100 cm³ of acetone, and 4 g of the compound obtained in Step B are refluxed for 18 hours.

The solvent is evaporated off in vacuo, and the residue is taken up in ethyl acetate and then extracted with 3N hydrochloric acid. The acidic phase separated off is rendered basic with sodium hydroxide and then extracted with ethyl acetate. The extract is washed until neutral, dried over anhydrous magnesium sulphate and then evaporated in vacuo to yield 4.5 g of an oil which is purified on a column of silica using a mixture of methylene chloride and methanol (90:10 v/v) as eluant.

Yield: 64%

Spectral characteristics: NMR (CDCl₃) 6.7 ppm, singlet, 4H; 6.8 and 6.65 ppm, 2 doublets, 2H; 3.85 ppm, singlet, 12H; 3.65 ppm, multiplet, 3H; 3.45 ppm, singlet, 2H; 3.2 ppm, doublet, 1H; 2.7-2.1 ppm, multiplet, 5H; 2.25 ppm, singlet, 3H; 1.7 ppm, singlet, 2H.

STEP D:
(R,S)-7,8-dimethoxy-3-{3-{N-[(4,5-dimethoxybenzocyclobut-1-yl)methyl]-N-(methyl)amino)propyl)-1,3,4,5-tetrahydro-2H-3-benzazepin-2-one 5 g of the compound obtained in Step C in 50 cm³ of glacial acetic acid are hydrogenated in a Parr apparatus under a hydrogen pressure of $49 \times 10^4$ Pa at room temperature for 24 hours in the presence of 1 g of 10% palladium hydroxide. The catalyst is filtered off, the solvent is evaporated off, and then the dry residue is taken up in water and ethyl acetate. The aqueous phase separated off is rendered basic with sodium hydroxide and then extracted with ethyl acetate. The organic phase is dried over anhydrous magnesium sulphate and concentrated in vacuo; the residue is then purified on a column of silica using a mixture of methylene chloride and methanol (95:5 v/v) as eluant. Recrystallisation from ethyl acetate yields 2 g of the compound of the Example.

Yield: 40%.
Melting point: 101-103° C.

Spectral characteristics: NMR (CDCl₃) 6.7 ppm, 2 singlets, 2H; 6.55 ppm, 2 singlets, 2H; 3.9-3.6 ppm, 2 singlets and 1 triplet, 16 H; 3.5 ppm, multiplet, 3H; 3.25 ppm doublet, 1H; 3.05 ppm, triplet 2H; 2.8-2.3 ppm, doublet, multiplet and triplet, 5H; 2.3 ppm, singlet, 3H; 1.75 ppm multiplet, 2H.

EXAMPLE 2

(+)-7,8-dimethoxy-3-{3-{N-[(4,5-dimethoxybenzocyclobut-1-yl)methyl]-N-(methyl)amino)propyl)-1,3,4,5-tetrahydro-2H-3-benzazepin-2-one By proceeding as in Example 1, but using the optically active (+) form, resolved in the form of the (d)-camphosulphonate salt, of the compound obtained in Step A of Example 1, the following are obtained:

STEP A:
(+)-N-[(4,5-dimethoxybenzocyclobut-1-yl)methyl]-N-(methyl)amine

The (R,S)-N-[(4,5-dimethoxybenzocyclobut-1-yl)methyl]-N-(methyl)amine obtained in Step A of Example 1 is reacted with an equimolar amount of (d)-camphosulphonic acid in ethanol. After evaporation of the solvent in vacuo, the salt is recrystallised first in ethyl acetate and then in acetonitrile until the (+) enantiomer is obtained with an optical purity of greater than 99% (evaluation by high performance liquid chromatography on a CHIRALCEL ®OD column).

Melting point ((d)-camphosulphonate): 160°–162° C.
Rotatory power (concentration: 1% in DMSO):

| λnm | [α] 20.5 °C. |
|---|---|
| 589 | +32.0° |
| 578 | +33.7° |
| 546 | +39.7° |
| 436 | +83.9° |
| 365 | +195.6° |

STEP B:
7,8-dimethoxy-3-[3-iodopropyl]-1,3-dihydro-2H-3-benzazepin-2-one.

STEP C:
(+)-7,8-dimethoxy-3-{3-{N-[(4,5-dimethoxybenzocyclobut-1-yl)methyl]-N-(methyl)amino)propyl)-1,3-dihydro-2H-3-benzazepin-2-one.

The (d)-camphosulphonate salt of the compound obtained in Step A dissolved in ethyl acetate is initially rendered basic with sodium hydroxide, then the organic phase is separated, washed, dried over anhydrous sodium sulphate and evaporated before being reacted in accordance with Step C of Example 1.

STEP D: Dibenzoyltartrate of the (+) isomer of 7,8-dimethoxy-3-{3-{N-[(4,5-dimethoxybenzocyclobut-1-yl)methyl]-N-(methyl) amino)propyl)-1,3,4,5-tetrahydro-2H-3-benzazepin-2-one.

Melting point: 104°–106° C.
Recrystallisation solvent of the dibenzoyltartrate salt: H₂O
Rotatory power (base, concentration: 1% in CHCl₃);

| λnm | [α] 20.5° C. |
|---|---|
| 589 | +3.9° |
| 578 | +4.4° |
| 546 | +4.9° |
| 436 | +8.10° |
| 365 | insufficient energy |

STEP E: Monohydrochloride of the (+) isomer of 7,8-dimethoxy-3-{3-{N-[(4,5-dimethoxybenzocyclobut-1-yl)methyl]-N-(methyl)amino)propyl)-1,3,4,5-tetrahydro-2H-3-benzazepin-2-one 14.9 ml of 0.1N HCl are added to 0.7 g of (+)-7,8-dimethoxy-3-{3-{N-[(4,5-dimethoxybenzocyclobut-1-yl)methyl]-N-methyl-)amino)propyl)-1,3,4,5-tetrahydro-2H-3-benzazepin-2-one. The whole is stirred, filtered, concentrated and recrystallised from 5 ml of acetonitrile. 0.5 g of the corresponding monohydrochloride is obtained (yield: 55%).

Melting point (instantaneous): 135°–140° C.
Rotatory power (1% in DMSO):

| λnm | [α] 21° C. |
|---|---|
| 589 | +7.8° |
| 578 | +8.0° |
| 546 | +9.0° |
| 436 | +15.3° |
| 365 | +27.8° |

EXAMPLE 3

(−)-7,8-dimethoxy-3-{3-{N-[(4,5-dimethoxybenzocyclobut-1-yl) methyl]-N-(methyl)amino)propyl56-1,3,4,5-tetrahydro-2H-3-benzazepin-2-one Analogously to Example 2, but using the optically active (−) form, resolved in the form of the (1)-camphosulphonate salt, of the compound obtained in Step A of Example 1, the following are obtained:

STEP A:
(−)-N-[(4,5-dimethoxybenzocyclobut-1-yl)methyl]-N-(methyl)amine

Melting point ((I)-camphosulphonate) ; 160°–162° C.
Rotatory power (concentration 0.85% in DMSO):

| λnm | [α] 20.5° C. |
|---|---|
| 589 | −32.2° |
| 578 | −34.1° |
| 546 | −39.9° |
| 436 | −84.5° |
| 365 | −198.1° |

STEP B
7,8-dimethoxy-3-[3-iodopropyl]-1,3-dihydro-2H-3-benzazepin-2-one.

STEP C:
(−)-7,8-dimethoxy-3-{3-{N-[(4,5-dimethoxybenzocyclobut-1-yl)methyl]-N-(methyl)amino)propyl)-1,3-dihydro-2H-3-benzazepin-2-one.

STEP D: Dibenzoyltartrate of the (−) isomer of 7,8-dimethoxy-3-{3-{N-[(4,5-dimethoxybenzocyclobut-1-yl)methyl]-N-(methyl)amino)propyl}-1,3,4,5-tetrahydro-2H-3-benzazepin- 2-one.

Melting point (dibenzoyltartrate): 104°–106° C.
Recrystallisation solvent of the dibenzoyltartrate salt: H₂O
Rotatory power (concentration: 85% in DMSO):

| λnm | [α] 20.5° C. |
|---|---|
| 589 | −4.3° |
| 578 | −4.6° |
| 546 | −5.0° |
| 436 | −8.50° |
| 365 | insufficient energy |

STEP E: Monohydrochloride of the (−) isomer of 7,8-dimethoxy-3-{3{N-[(4,5-dimethoxybenzocyclobut-1-yl)methyl]-N-methyl)amino}propyl}-1,3,4,5-tetrahydro-2H-3-benzazepin-2-one.

By proceeding as in Example 2, Step E, the desired monohydrochloride is obtained in a 50% yield.
Melting point (instantaneous): 135°–140° C.
Rotatory power (1% in DMSO):

| λnm | [α] 21° C. |
|---|---|
| 589 | −6.0° |
| 578 | −6.2° |
| 546 | −7.2° |
| 436 | −13.5° |
| 365 | −26.5° |

EXAMPLE 4

(R,S)-7,8-dimethoxy-3-{3-{N-[(4,5-dimethoxybenzocyclobut-1-yl)methyl]amino}propyl}-1,3,4,5-tetrahydro-2H-3-benzazepin-2-one By proceeding as in Example 1, but replacing the ethyl chloroformate in Stage $A_2$ of Step A with benzoyl chloride, there are obtained in succession:

STEP A: R,S-N-{[4,5-dimethoxybenzocyclobut-1-yl]-methyl}-N-(benzyl)amine
Yield: 90.4%.

STAGE $A_1$ (R,S)-N-[(4,5-dimethoxybenzocyclobut-1-yl)methyl)amine hydrochloride.

STAGE $A_2$ (R,S)-N-([4,5-dimethoxybenzocyclobut-1-yl]methyl)-N-(benzoyl)amine.
Yield: 98%.
Melting point: 142°–144° C.

STEP B:

7,8-dimethoxy-3-[3-iodopropyl]-1,3-dihydro-2H-3-benzazepin-2-one.

STEP C:

(R,S)-7,8-dimethoxy-3-{3-{N-[(4,5-dimethoxybenzocyclobut-1-yl)methyl]-N-(benzyl)amino}propyl}-1,3-dihydro-2H-3-benzazepin-2-one.
Yield: 62%.

STEP D (R,S)-7,8-dimethoxy-3-{3-{N-[(4,5-dimethoxybenzocyclobut-1-yl)methyl)amino}propyl}-1,3,4,5-tetrahydro-2H-3-benzazepin-2-one.

Melting point (dihydrochloride): 185°–188° C.
Recrystallisation solvent of the dihydrochloride salt: ethyl acetate.

EXAMPLE 5

(R,S)-7,8-dimethoxy-3-{3-{N-[2-(4,5-dimethoxybenzocyclobut-1-yl)ethyl]amino}propyl}-1,3,4,5-tetrahydro-2H-3-benzazepin-2-one By proceeding as in Example 1, but replacing the (R,S)-1-(cyano)-4,5-(dimethoxy)benzocyclobutane in Stage $A_1$ with (R,S)-(4,5-dimethoxybenzocyclobut-1-yl)acetonitrile, and the ethyl chloroformate in Stage $A_2$ with benzoyl chloride, the following are obtained:

STEP A:

(R,S)-N-[2-(4,5-dimethoxybenzocyclobut-1-yl)-ethyl]-N-(benzyl)amine.
Yield: 70%

STAGE $A_1$ (R,S)-N-[2-(4,5-dimethoxybenzocyclobut-1-yl)ethyl]amine hydrochloride.
Yield: 41%

STAGE $A_2$ (R,S)-N-[2-(4,5-dimethoxybenzocyclobut-1-yl)ethyl]-N-(benzoyl)amine.
Yield: 98%

STEP B 7,8-dimethoxy-3-[3-iodopropyl]-1,3-dihydro-2H-3-benzazepin-2-one.

STEP C:

(R,S)-7,8-dimethoxy-3-{3-{N-[2-(4,5-dimethoxybenzocyclobut-1-yl)ethyl]-N-(benzyl)amino}propyl}-1,3-dihydro-2H-3-benzazepin-2-one.
Yield: 48%

STEP D:

(R,S)-7,8-dimethoxy-3-{3-{N-[2-(4,5-dimethoxybenzocyclobut-1-yl)ethyl)amino}propyl}-1,3,4,5-tetrahydro-2H-3-benzazepin-2-one.

Melting point (acetate): 98°–102° C.
Recrystallisation solvent of the acetate salt: diisopropyl ether.

EXAMPLE 6

(R,S)-7,8-dimethoxy-3-{3-{N-[2-(4,5-dimethoxybenzocyclobut-1-yl)ethyl]-N-(methyl)azino)propyl)-1,3,4,5-tetrahydro-2H-3-benzazepin-2-one By proceeding as in Example 1, but replacing the (R,S)-1-(cyano)-4,5-(dimethoxy)benzocyclobutane in Stage $A_1$ with (R,S)-(4,5-dimethoxybenzocyclobut-1-yl)acetonitrile, there are obtained in succession:

STEP A:

R,S-N-[2-(4,5-dimethoxybenzocyclobut-1-yl)-ethyl]-N-(methyl)amine.
Yield: 68%

STAGE $A_1$ (R,S)-N-[2-(4,5-dimethoxybenzocyclobut-1-yl)ethyl)amine hydrochloride.

STAGE $A_2$ (R,S)-N-[2-(4,5-dimethoxybenzocyclobut-1-yl)ethyl]-N-(ethoxycarbonyl)amine.
Yield: 98%.

STEP B:

7,8-dimethoxy-3-[3-iodopropyl]-1,3-dihydro-2H-3-benzazepin-2-one.

STEP C:

(R,S)-7,8-dimethoxy-3-{3-{N-[2-(4,5-dimethoxybenzocyclobut-1-yl)ethyl)-N-(methyl)amino}propyl}-1,3-dihydro-2H-3-benzazepin-2-one.
Yield: 62%

STEP D:
(R,S)-7,8-dimethoxy-3-{3-{N-[2-(4,5-dimethoxybenzocyclobut-1-yl)ethyl]-N-(methyl)amino}propyl}-1,3,4,5-tetrahydro-2H-3-benzazepin-2-one.

Melting point (dihydrochloride): 102°–105° C.
Recrystallisation solvent of the dihydrochloride salt: diethyl ether.

EXAMPLE 7

(R,S)-7,8-dimethoxy-3-{3-{N-[(5-methoxybenzoeyclobut-1-yl)methyl]-N-(methyl)amino}propyl}-1,3,4,5-tetrahydro-2H-3-benzazepin-2-ons By proceeding as in Example 1, but replacing the (R,S)-1-(cyano)-4,5-(dimethoxy)benzocyclobutane in Stage A₁ with (R,S)-1-(cyano)-5-(methoxy)benzoeyclobutane, there are obtained in the last two Steps:

STEP C: (R,S)-7,8-dimethoxy-3-{3-{N-[(5-methoxybenzo-cyclobut-1-yl)methyl]-N-(methyl)amino}propyl}-1,3-dihydro-2H-3-benzazepin-2-one.

STEP D:
(R,S)-7,8-dimethoxy-3-{3-{N-[(5-methoxybenzocyclobut-1-yl)methyl)-N-(methyl)amino}propyl}-1,3,4,5-tetrahydro-2H-3-benzazepin-2-one.

Yield: 48%.
Melting point (dihydrochloride): 125°–130° C.
Recrystallisation solvent of the dihydrochloride salt: ethyl acetate.

EXAMPLE 8

(R,S)-7,8-dimethoxy-3-{3-[(benzocyclobut-1-yl)methyl]-N-(methyl)amino}propyl}-1,3,4,5-tetrahydro-2H-3-benzazepin-2-one.

By proceeding as in Example 1, but replacing the (R,S)-1-(cyano)-4,5-(dimethoxy)benzocyclobutane in Stage A₁ with (R,S)-1-(cyano)benzocyclobutane, there are obtained in the last two Steps:

STEP C:
(R,S)-7,8-dimethoxy-3-(3-[(benzocyclobut-1-yl)methyl]-N-(methyl)amino}propyl}-1,3-dihydro-2H-3-benzazepin-2-one.

STEP D:
(R,S)-7,8-dimethoxy-3-(3-[(benzocyclobut-1-yl)methyl]-N-(methyl)amino}propyl}-1,3,4,5-tetrahydro-2H-3-benzazepin-2-one.

Yield: 45%.
Melting point (dihydrochloride): 128°–132° C.
Recrystallisation solvent of the dihydrochloride salt: ethyl acetate.

EXAMPLE 9

7,8-dimethoxy-3-{3-{N-[(5,6-dimethoxyindan-2-yl)methyl]-N-(methyl)amino}propyl}-1,3,4,5-tetrahydro-2H-3-benzazepin-2-one.

STEP A:
N-[(5,6-dimethoxyindan-2-yl)methyl)-N-(methyl)-amine.

STAGE A₁:
5,6-(dimethoxy)-2-(ethoxycarbonyl)-indan-1-one.

0.5 cm³ of diethyl carbonate are added to a suspension of 20 g of 50% sodium hydride (previously washed with hexane) in 240 cm³ of tetrahydrofuran. The whole is refluxed for 1½ hours, then a solution of 40 g of 5,6-dimethoxyindan-1-one in 440 cm of tetrahydrofuran is added at room temperature. The whole is again refluxed for 3 hours, then the reaction mixture is cooled, diluted with ethyl acetate, and treated with an aqueous acetic acid solution. The organic phase is separated off, dried over anhydrous magnesium sulphate, and then concentrated in vacuo to yield 52 g of the desired compound.
Yield: 98%.
Melting point: 132°–134° C.

STAGE A₂

(5,6-dimethoxyindan)-2-oic acid.

117 g of zinc and 11.7 g of mercuric chloride are added, with stirring, to a mixture composed of 195 cm³ of concentrated hydrochloric acid in 105 cm³ of water and 52 g of the compound obtained in Stage A₁ in 520 cm³ of toluene.

The reaction mixture is refluxed for 24 hours and cooled, and the toluene phase is separated off and then extracted with a 1N sodium hydroxide solution. After separating off the aqueous phase is acidified with 1N hydrochloric acid and then extracted with ethyl acetate, and subsequently the organic phase is separated off and dried over anhydrous magnesium sulphate and then filtered and concentrated in vacuo to yield 20 g of the desired compound. The toluene phase obtained earlier is evaporated in vacuo to yield 19 g of 5,6-dimethoxy-2-ethoxycarbonylindane, which is reacted for 18 hours at room temperature, with stirring, in the presence of 80 cm³ of ethanol and 80 cm³ of 1N sodium hydroxide. The whole is evaporated to dryness, then acidified with 1N hydrochloric acid, extracted with ethyl acetate and concentrated in vacuo to yield 14.8 g of the desired compound which are combined with the 20 g obtained earlier.
Yield: 78%.
Melting point: 126°–128° C.

STAGE A₃

N-[(5,6-dimethoxyindan-2-yl)carbonyl]-N-(methyl)amine.

10.2 g of carbonyldiimidazole are added in portions to a solution of 14 g of the compound obtained in Stage A₂ in 150 cm³ of methylene chloride and the whole is stirred for 4 hours. The solution is saturated with methylamine for 4 hours, with stirring, at room temperature. The reaction mixture is diluted with water. The organic phase is separated off, washed with 1N sodium hydroxide, separated off again, dried over anhydrous magnesium sulphate and evaporated to dryness to yield the desired compound, which is recrystallised from ethanol.
Melting point: 170°–172° C.

STAGE A₄

N-[(5,6-dimethoxyindan-2-yl)methyl]-N-(methyl)amine.

10.5 g of the compound obtained in Stage A in 150 cm³ of tetrahydrofuran are added to a suspension of 1.7 g of lithium aluminium hydride in 25 cm³ of tetrahydrofuran. The reaction mixture is refluxed for 24 hours then a hydrolysis step is carried out by adding 1.1 cm³ of water followed by 0.94 cm³ of 20% sodium hydroxide and finally by 4.2 cm³ of water. The whole is filtered and the solvent is evaporated off in vacuo to yield 3.9 g of an oil which corresponds to the compound in the title.

Yield: 40%.

STEP B:

7,8-dimethoxy-3-[3-iodopropyl)-1,3-dihydro-2H-3-benzazepin-2-one.

Preparation identical to that of Step B of Example 1.

STEPS C and D: By proceeding as in Steps C and D of Example 1, but replacing in Step C the compound obtained in Step A of Example 1 by the compound obtained in Step A of the current Example, there are obtained in succession:

STEP C: 7,8-dimethoxy-3-{3-{N-[(5,6-dimethoxyindan-2-yl)methyl]-N-(methyl)amino}propyl}-1,3-dihydro-2H-3-benzazepin-2-one.

Yield: 61% (oil).

Spectral characteristics: NMR (CDCl$_3$): 6.75 ppm, 3 singlets, 4H; 6.3–6.1 ppm, 2 doublets, 2H; 3.9 ppm, 2 singlets, 12H; 3.6 ppm triplet, 2H; 3.4 ppm, singlet, 2H; 3.4 ppm, singlet, 2H; 3 ppm, multiplet 2H; 2.7–2.5 ppm, 2 multiplets, 3H; 2.25 ppm, 2 multiplets, 4H; 2.15 ppm, singlet, 3H; 1.7 ppm, multiplet, 2H.

STEP D: 7,8-dimethoxy-3-{3-{N-[(5,6-dimethoxyindan-2-yl)methyl]-N-(methyl)amino}propyl}-1,3,4,5-tetrahydro-2H-3-benzazepin-2-one.

Yield: 44%.

Melting point: 98°–100° C.

Recrystallisation solvent: ethyl acetate.

Spectral characteristics: NMR (CDCl$_3$) 6.7 ppm, singlet, 2H; 6.55 ppm, singlet, 1H; 3.85 ppm, singlet, 12H; 3.8 ppm multiplet, 2H; 3.75 ppm multiplet, 2H; 3.5 ppm, triplet, 2H; 3.25 ppm, quintuplet, 1H; 3.05 ppm, multiplet, 2H; 2.8 ppm, multiplet, 4H; 2.4 ppm, multiplet, 2H; 2.25 ppm, singlet, 3H; 1.8 ppm, quintuplet, 2H.

EXAMPLE 10

7,8-dimethoxy-3-{3-{N-[(5,6-dimethoxyindan-2-yl)methyl]-amino}propyl56
-1,3,4,5-tetrahydro-2H-3-benzazepin-2-one.

By proceeding as in Example 9, but replacing the methylamine in Step A$_3$ with ammonia, there are obtained in succession:

STEP A: N-[(5,6-dimethoxyindan-2-yl)methyl]amine.

STAGE A$_1$ 5,6-(dimethoxy)-2-(ethoxycarbonyl)-indan-1-one.

STAGE A$_2$ (5,6-dimethoxyindan)-2-oic acid.

STAGE A$_3$ (5,6-dimethoxyindan-2-yl)carboxamide.

Yield: 85.4%

Melting point 190°–192° C.

STEP B:

7,8-dimethoxy-3-[3-iodopropyl]-1,3-dihydro-2H-3-benzazepin- 2-one.

STEP C:

7,8-dimethoxy-3-{3-{N-[(5,6-dimethoxyindan-2-yl)methyl]amino}propyl}-1,3-dihydro-2H-3-benzazepin-2-one.

Yield: 33% (oil).

STEP D:

7,8-dimethoxy-3-{3-{N-[(5,6-dimethoxyindan-2-yl)methyl)amino}propyl}-1,3,4,5-tetrahydro-2H-3-benz-azepin-2-one.

Melting point: 86°–94° C.

Recrystallisation solvent: ethyl acetate.

Spectral characteristics: NMR (CDCl$_3$): 6.7 ppm, singlet, 2H; 6.6 ppm, singlet, 1H; 6.55 ppm, singlet, 1H; 3.8 ppm, singlet, 14H; 3.7 ppm, multiplet, 2H; 3.5 ppm, triplet, 2H; 3.05 ppm, multiplet, 2H; 3.0 ppm, multiplet, 2H; 2.9–2.5 ppm, multiplet, 7H; 1.8 ppm, quintuplet, 2H.

EXAMPLE 11

7,8-dimethoxy-3-{3-{N-[(4--methoxybenzocyclobut-1-yl)-methyl]-N-(methyl)amino}propyl}-1,3,4,5-tetrahydro-2H-3-benzazepin-2-one.

By operating as in Example 1: 11 g of N-[(4-methoxybenzocyclobut-1-yl)methyl]-N-(ethoxycarbonyl)amine (theoretical yield) are obtained from 8.7 g of N-[(4-methoxybenzocyclobut-1-yl)methyl]amine hydrochloride, 4.2 ml of ethyl chloroformate, 12 ml of triethylamine and 90 ml of dichloromethane.

From 11 g of that product, 3.3 g of LiAlH$_4$ and 160 ml of tetrahydrofuran heated at reflux for 6 hours, 7 g of N-[(4-methoxybenzocyclobut-1-yl)methyl)-N-(methyl)amine (yield 90%) are obtained.

From 15 g of 7,8-dimethoxy-3-[3-iodopropyl]-1,3-dihydro-2H-3-benzazepin-2-one, 7 g of N-[(4-methoxybenzocyclobut-1-yl)methyl]-N-(methyl)amine, 22 g of K$_2$CO$_3$ and 300 ml of acetone, there are obtained 17.5 g (theoretical yield) of 7,8-dimethoxy-3-{3-{N-[(4-methoxybenzocyclobut-1-yl)-methyl)-N-(methyl)amino}propyl}-1,3-dihydro-2H-3-benzazepin-2-one.

From 5 g of that product, 60 ml of ethanol, 1 ml of acetic acid and 3 g of palladium hydroxide, there are obtained 1.9 g of 7,8-dimethoxy-3-{3-{N-[(4-methoxybenzocyclobut-1-yl)methyl]-N-(methyl)amino}propyl}-1,3,4,5-tetrahydro-2H-3-benzazepin.-2-one (yield: 65%), which is converted into the corresponding dihydrochloride which, recrystallised from acetonitrile, melts at 160°–164° C.

EXAMPLE 12

7,8-dimethoxy-3-{3-{N-[2-(5,6-dimethoxyindan-2-yl)-ethyl]-N-(methyl)amino}propyl}-1,3,4,5-tetrahydro-2H-3-benzazepin-2-one.

By proceeding as in Example 9: From 45 g of 5,6-dimethoxyindan-2-oic acid and 7.7 g of LiAlH$_4$ there are obtained, after 18 hours at room temperature followed by hydrolysis and concentration, 35 g of (5,6-dimethoxyindan-2-yl)methanol (yield: 85%).

From 10 g of the alcohol so-obtained, 13 g of paratoluenesulphonyl chloride and 100 ml of pyridine, which are maintained for 2 hours at 0° C. and then for 12 hours at 20° C., and subsequently washed with water and concentrated, 15 g of the corresponding para-toluenesulphonate are obtained. The latter, treated with 6 g of NACN in 105 ml of DMSO for 8 hours at 80° C. then concentrated and taken up in water/diethyl ether, produces in a yield of 82% 9 g of (5,6-dimethoxyindan-2-yl)methyl cyanide.

From 25 g of (5,6-dimethoxyindan-2-yl)methyl cyanide, heated at reflux for 18 hours with 20 g of KOH, 250 ml of ethanol and 31 ml of water, and after concentration of the reaction mixture, acidification and extraction, 24 g of (5,6-dimethoxyindan-2-yl)acetic acid are obtained.

From 31 g of (5,6-dimethoxyindan-2-yl)acetic acid, 400 ml of methylene chloride and 21.3 g of carbonyldiimidazole, stirred together for 2 hours at room temperature, and after saturation of the reaction mixture with methylamine for 4 hours and finally washing with water and concentration, 33 g of N-[(5,6-dimethoxyindan-2-yl)methylcarbonyl]-N-(methyl)amine are obtained (theoretical yield).

37 g of N-[(5,6-dimethoxyindan-2-yl)methylcarbonyl]-N-(methyl)amine are treated with 8.5 g of LiAlH$_4$ in 470 ml of tetrahydrofuran under reflux for 6 hours, then the mixture is hydrolysed and subsequently concentrated to yield, finally, 24 g of N-[(5,6-dimethoxyindan-2-yl)-ethyl)-N-(methyl)amine (yield 69%).

From 7 g of the amine so-obtained, 8.7 g of 7,8-dimethoxy-3-[3-iodopropyl]-1,3-dihydro-2H-3-benzazepin-2-one, 400 ml of methyl cyanide and 16.5 g of potassium carbonate, 12.5 g of 7,8-dimethoxy-3-{3-{N-[(4,5-dimethoxyindan-2-yl)ethyl]-N-(methyl)amino}propyl}-1,3-dihydro- 2H-3-benzazepin-2-one (yield 85%) are obtained. The latter, added to 180 ml of ethanol and 6 ml of acetic acid, is hydrogenated in the presence of 6 g of palladium hydroxide to yield 7,8-dimethyl-3-{3-{N-[2-(5,6-dimethoxyindan-2-yl)ethyl]-N-(methyl)amino}propyl}-1,3,4,5-tetrahydro-2H-3-benzazepin-2-one, m.p. (KM): 102–107° C. (diisopropyl ether) (yield: 7%).

EXAMPLE 13

7,8-dimethoxy-3-{3-{N-[(4,5-dimethoxy-1-methylbenzocyclobut-1-yl)methyl]-N-(methyl)amino)propyl)-1,3,4,5-tetrahydro-2H-3-benzazepin-2-one.

By operating as in Example 9: From 20 g of 4,5-dimethoxybenzocyclobut-1-yl cyanide, 35 ml of diisopropylamine, 2.5 mol of butyllithium in 100 ml of hexane, 170 ml of tetrahydrofuran and 123 ml of methyl iodide, 22 g of 4,5-dimethoxy-1-methylbenzocyclobut-1-yl cyanide are obtained in the form of oil (yield 97%) which, treated for 4 hours under reflux with 17.5 g of potassium hydroxide, 220 ml of ethanol and 27 ml of water, and after concentration of the mixture, acidification and extraction with ethyl acetate, yield 20 g of 4,5-dimethoxy-1-methylbenzocyclobutan-1-oic acid in the form of oil (yield 92%).

The 20 g of acid are stirred for one night with 14.6 g of carbonyldiimidazole in 200 ml of methylene chloride, then the whole is saturated with 15 g of methylamine. After washing with water and concentration, 9.7 g of N-[(4,5-dimethoxy-1-methylbenzocyclobut-1-yl)carbonyl]-N-methylamine (yield 47.6%) are obtained, which are treated for 24 hours at room temperature and then for 4 hours under reflux with 2.6 g of LiAlH$_4$ in 140 ml of tetrahydrofuran to yield, after hydrolysis of the reaction mixture by means of water and sodium hydroxide solution followed by concentration, 9 g of N-[(4,5-dimethoxy-1-methylbenzocyclobut-1-yl)methyl)-N-(methyl)amine (yield 95%).

From 4.4 g of the amine so-obtained and 7.7 g of 7,8-dimethoxy-3-[3-iodopropyl)-1,3-dihydro-2H-3-benzazepin-2-one in 160 ml of acetone in the presence of 9.1 g of potassium carbonate, by proceeding as in Example 1, Step C, 12.4 g of 7,8-dimethoxy-3-{3-{N-[(4,5-dimethoxy-1-methylbenzocyclobut-1-yl)methyl]-N-(methyl)amino)-propyl}-1,3-dihydro-2H-3-benzazepin-2-one (yield 95%) are obtained.

From 12 g of the latter product, 125 ml of ethanol, 2.6 ml of acetic acid and 6 g of palladium hydroxide there are obtained, by proceeding as in Example 1 Step D, 3.3 g of 7,8-dimethoxy-3-{3-{N-[(4,5-dimethoxy-1-methylbenzocyclobut-1-yl)methyl]-N-(methyl)amino}propyl}-1,3,4,5-tetrahydro-2H-3-benzazepin-2-one, m.p. (KM): 105°–108° C.

EXAMPLE 14

7,8-dimethoxy-3-{3-{N-[(furo[2,3-b]benzocyclobut-6-yl)-methyl]-N-(methyl)azino)propyl)-1,3,4,5-tetrahydro-2H-3-benzazepin-2-one.

From 25 g of [(5-methoxybenzocyclobut-1-yl)methyl]amine hydrochloride, treated for one night, with stirring, with 41.7 ml of triethylamine and 10.6 ml of acetyl chloride in 300 ml of methylene chloride, 25.8 g of N-[(5-methoxybenzocyclobut-1-yl)methyl]-N-acetylamine (oil) are obtained (theoretical yield).

25.6 g of the product so-obtained in 375 ml of CHCl$_3$ are treated with stirring, at 0° C., for 2 hours with 130 ml of BBr$_3$ then, after the addition of ethanol, concentration and washing, 23 g of N-[(5-hydroxybenzocyclobut-1-yl)methyl]-N-acetylamine (oil) are obtained (yield 98%).

The whole of the product obtained is treated for 4 hours at 0° C. with 13 ml of ClCH$_2$CN, 297 ml of a molar solution of BCl$_3$ in CH$_2$Cl$_2$ and 16.6 g of AlCl$_3$ in 65 ml of CH$_2$Cl$_2$.

The whole is then washed with water and subsequently concentrated to yield 21 g of N-[3-oxo-2,3-dihydrofuro-[2,3-b]benzocyclobut-6-yl)methyl]-N-acetylamine, oil (yield 75%).

These 21 g of product are treated for 17 hours at room temperature with 6.4 g of NaBH$_3$ in 210 ml of methanol and 110 ml of NaHCO$_3$. After dilution of the mixture with HCl and then extraction with ethyl acetate, 15.8 g of N-[furo[2,3-b)benzocyclobut-6-ylmethyl]-N-acetylamine, m.p. (KM): 100°–102° C. (yield 75%) are obtained.

These 15.8 g of amine are maintained at reflux for 20 hours with 700 ml of methanol, 220 ml of concentrated HCl and 220 ml of water. The reaction mixture is then concentrated and taken up in CH$_3$CN to yield 9.3 g of N-[(furo[2,3-b]benzocyclobut-6-yl)methyl]amine hydrochloride, m.p. (KH): 268°–270° C. (yield 60%).

2.25 g of this hydrochloride are reacted for 21 hours at room temperature with 1.13 ml Of ClCOOC$_2$H$_5$, 3.3 ml of triethylamine and 3.3 ml of methylene chloride. After washing with water and concentration, 1.65 g of N-[(furo[2,3-b]benzocyclobut-6-yl)-methyl]-N-(ethoxycarbonyl)amine, oil (yield 69%) are obtained.

The whole of this product is treated for 6 hours at reflux with 0.5 g of LiAlH$_4$ in 30 ml of tetrahydrofuran; the reaction mixture is then hydrolysed and subsequently concentrated to yield 1.3 g of N-[(furo[2,3-b]benzocyclobut-6-yl)methyl]-N-methylamine (theoretical yield).

1.2 g of N-[(furo[2,3-b]benzocyclobut-6-yl)methyl]-N-methylamine, 1.9 g of 7,8-dimethoxy-3-(3-chloropropyl)-1,3,4,5-tetrahydro-2H-3-benzazepin-2-one and 13 ml of triethylamine are heated for 3 hours at 60° C., then for 1 hour at reflux. After extracting and washing the reaction mixture with sodium hydroxide, 1 g of 7,8-dimethoxy-3-{3-{N-[(furo[2,3-b]benzocyclobut-6-yl)-methyl]-N-(methyl)amino}propyl}-1,3,4,5-tetrahydro-2H-3-benzazepin-2-one (yield 31%) is obtained, m.p. (KM) of the corresponding dihydrochloride: 180°–188° C.

EXAMPLE 15

PHARMACOLOGICAL STUDY

A - IN VIVO STUDY

Haemodynamic effects of the compounds of the invention in conscious rats

Study protocol

Male Wistar rats (350–400 g) are anaesthetized by the intraperitoneal administration of a mixture of ketamine (Imalgene ® 1000; 140 mg/kg) and acepromazine (Veratranquil ® 1%; 14 mg/kg). The femoral artery and the jugular vein are catheterised for the measurement of the arterial pressure and the cardiac frequency, and for the intravenous injection of the test compounds, respectively. The animals are used after a post-operative period of 48 hours.

On the day of the experiment, a one hour stabilisation period is observed for the haemodynamic parameters. The treatments are administered by the intravenous route or the oral route. A control group receives the solvent used, under the same experimental conditions. The cardia frequency and the mean arterial pressure are continuously monitored until 6 hours after treatment has been administered.

Results

Effect of the compounds of the invention, administered by the intravenous route, on the cardiac frequency (CF) of conscious rats

| | Doses (mg/kg) | CF change (Δ%) | | | |
|---|---|---|---|---|---|
| | | 30 min | 1 h | 4 h | 6 h |
| Control | | 1 ± 2 | 2 ± 2 | −3 ± 1 | −5 ± 1 |
| Example 1 | 0.5 | −9 ± 4 | −10 ± 2 | −12 ± 4 | −17 ± 3 |
| | 1 | −18 ± 3 | −21 ± 3 | −16 ± 5 | −16 ± 3 |
| | 2 | −29 ± 2 | −26 ± 3 | −14 ± 2 | −16 ± 1 |
| Example 9 | 0.5 | −14 ± 4 | −16 ± 5 | −12 ± 3 | −14 ± 2 |
| | 1 | −31 ± 6 | −32 ± 7 | −21 ± 5 | −21 ± 4 |
| | 2 | −34 ± 3 | −35 ± 4 | −24 ± 4 | −24 ± 4 |

Effect of the compounds of the invention, administered by the oral route, on the cardiac frequency (CF) of conscious rats

| | Doses (mg/kg) | CF change (Δ%) | | |
|---|---|---|---|---|
| | | 1 h | 3 h | 6 h |
| Control | | −4 ± 1 | −3 ± 1 | −8 ± 1 |
| Example 1 | 1.5 | −14 ± 4 | −19 ± 4 | −19 ± 2 |
| | 3 | −22 ± 4 | −28 ± 3 | −26 ± 1 |
| | 6 | −14 ± 3 | −26 ± 3 | −29 ± 4 |
| Example 9 | 1.5 | −10 ± 5 | −13 ± 5 | −19 ± 4 |
| | 3 | −15 ± 2 | −31 ± 3 | −35 ± 3 |
| | 6 | −16 ± 3 | −27 ± 5 | −37 ± 3 |

The compounds of the invention have a powerful bradycardic activity of long duration both after administration by the intravenous route and after administration by the oral route.

This effect on the cardiac frequency is not accompanied by a detrimental effect on the arterial pressure.

The hearts of male Wistar rats (325–350 g) anaesthetized with sodium pentobarbital (30 mg/kg i.p.) are quickly removed, and the right auricles are isolated and connected to a Statham ® pressure sensor (UC$_2$-Gould) with an initial pressure of 0.5 g. The frequency of the spontaneous contractile activity is measured using a Biotach-Gould meter.

The physiological solution employed has the following composition (mM): NaCl 112; KCl 5; KH$_2$PO$_4$ 1; MgSO$_4$ 1.2; CaCl$_2$ 2.5; NaHCO$_3$ 25; glucose 11.5; EDTA 0.026; pH 7.4.

It is aerated with a mixture of 95% O$_2$/5% CO$_2$ and maintained at 35° C.

After 30 minutes' stabilisation, cumulative concentrations of the test compounds are added to the medium every 30 minutes.

Results

The compounds of the invention have a very marked reducing effect, which is concentration-dependent, on the spontaneous frequency of the isolated right auricles.

By way of example, the compounds of Examples 1 and 9 reduce the frequency of the auricles by 43% and 68% at a concentration of $3 \times 10^{-6}$ M.

These experiments show that the bradycardic activity of the compounds of the invention result in a direct effect on the sino-auricular node responsible for the cardiac pacemaker activity.

We claim:

1. A compound selected from those of formula I

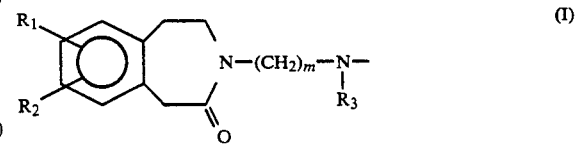

in which
m represents 2 to 5 inclusive,
n represents 1 to 6 inclusive,
p and q, which are the same or different, each represents 0, 1 or 2,
with the proviso that the sum of p and 2 is equal to 1 or 2,
R$_1$ and R$_2$, which are the same or different, each is selected from:
hydrogen,
halogen,
hydroxy,
lower alkoxy,
phenyl-lower alkoxy,
and substituted phenyl-lower alkoxy,
or R$_1$ and R$_2$, when they are carried by 2 adjacent carbon atoms, together form —O—(CH$_2$)$_r$—O— in which r represents 1 or 2,
R$_3$ is selected from:
hydrogen,
lower alkyl,
lower alkenyl,
cycloalkyl,
cycloalkyl-lower alkyl,
phenyl-lower alkyl,
substituted phenyl-lower alkyl,
—CO—R$_5$ or —CO—O—R$_5$
R$_5$ being selected from: hydrogen, lower alkyl, lower alkenyl, lower alkynyl, phenyl, substituted phenyl, phenyl-lower alkyl, substituted phenyl-lower alkyl, cyclo alkyl, and cycloalkyl-lower alkyl, and —CO—NR₆R₇ wherein R₆ and R₇ are the same or different and each has the same meanings as R₅ as defined above, or R₆ and R₇, with the nitrogen atom carrying them, together a saturated heterocyclic ring having 4 to 7 ring members, inclusive, all members except the nitrogen being carbon R₄ represents hydrogen or lower alkyl;

X, Y and Z, which are the same or different, are each selected from:
hydrogen,
halogen,
hydroxy,
lower alkoxy,
and substituted phenyl-lower alkoxy, or X and Y, or Y and Z, when they are carried by 2 adjacent carbon atoms, together form —O—(CH₂)ᵣ—O— (in which r is 1 or 2), —O—(CH₂)2— or —O—CH=CH—;

the term "substituted" describing the groups "phenyl" phenyl-lower alkyl" and "phenyl-lower alkoxy" meaning that those groups may be substituted in the phenyl nucleus by one or more substituents selected from halogen, hydroxy, trifluoromethyl, lower alkyl, and lower alkoxy, the terms "lower alkyl" and "lower alkoxy" meaning saturated linear or branched groups containing 1 to 6 carbon atoms inclusive, the terms "lower alkenyl" and "lower alkynyl" meaning unsaturated linear or branched groups containing 2 to 6 carbon atoms inclusive, the term "cycloalkyl" meaning a saturated hydrocarbon ring containing 3 to 8 inclusive, carbon atom in the ring, its possible optical isomers, as well as its addition salts with a pharmaceutically-acceptable acid.

2. A compound of claim 1, which is selected from (R,S)-7,8-dimethoxy-3-{3-{N-[(4,5-dimethoxybenzocyclobut-1-yl)methyl]-N-(methyl)amino}propyl}-1,3,4,5-tetrahydro-2H-3-benzazepin-2-one, its optical isomers, isolated or in the form of a mixture, and its addition salts with a pharmaceutically acceptable acid.

3. A compound of claim 1, which is selected from (R,S)-7,8-dimethoxy-3-{3-{N-[(5-methoxybenzocyclobut-1-yl)methyl]-N-(methyl)amino}propyl}-1,3,4,5-tetrahydro-2H-3-benzazepin-2-one, its optical isomers, isolated or in the form of a mixture, and its addition salts with a pharmaceutically-acceptable acid.

4. A compound of claim 1, which is selected from (R,S)-7,8-dimethoxy-3-{3-{N-[(benzocyclobut-1-yl)methyl]-N-(methyl)amino}propyl}-1,3,4,5-tetrahydro-2H-3-benzazepin-2-one, its optical isomers, isolated or in the form of a mixture, and its addition salts with a pharmaceutically-acceptable acid.

5. A compound of claim 1, which is selected from 7,8-dimethoxy-3-(3-(N-[(5,6-dimethoxyindan-2-yl)methyl]-N-(methyl)amino)propyl}-1,3,4,5-tetrahydro-2H-3-benzazepin-2-one, and its addition salts with a pharmaceutically-acceptable acid.

6. A compound of claim 1, which is selected from 7,8-dimethoxy-3-{3-{N-[(5,6-dimethoxyindan-2-yl)methyl]amino}propyl}-1,3,4,5-tetrahydro-2H-3-benzazepin-2-one, and its addition salts with a pharmaceutically-acceptable acid.

7. A compound of formula (IV):

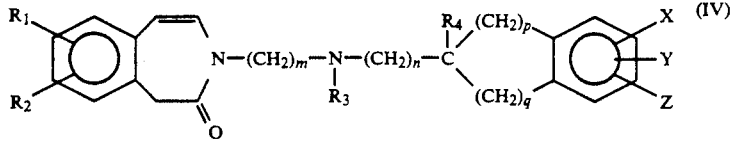

in which
m represents 2 to 5 inclusive,
n represents 1 to 6 inclusive,
p and q, which are the same or different, each represents 0, 1 or 2,
with the proviso that the sum of p and 2 is equal to 1 or 2, R₁ and R₂, which are the same or different, each is selected from:
hydrogen,
halogen,
hydroxy,
lower alkoxy,
phenyl-lower alkoxy,
and substituted phenyl-lower alkoxy, or R₁ and R₂, when they are carried by 2 adjacent carbon atoms, together form —O—(CH₂)ᵣ—O— in which r represents 1 or 2, R₃ is selected from:
hydrogen,
lower alkyl,
lower alkenyl,
cycloalkyl,
cycloalkyl-lower alkyl,
phenyl-lower alkyl,
substituted phenyl-lower alkyl,
—CO—R₅ or —CO—O—R₅

R₅ being selected from: hydrogen, lower alkyl, lower alkenyl, lower alkynyl, phenyl, substituted phenyl, phenyl-lower alkyl, substituted phenyl-lower alkyl, cyclo alkyl, and cycloalkyl-lower alkyl, and —CO—NR₆R₇ wherein R₆ and R₇ are the same or different and each has the same meanings as R₅ as defined above, or R₆ and R₇, with the nitrogen atom carrying them, together form a saturated heterocyclic ring having 4 to 7 ring members, inclusive, R₄ represents hydrogen or lower alkyl; all members except the nitrogen being carbon X, Y and Z, which are the same or different, are each selected from:
hydrogen,
halogen,
hydroxy,
lower alkoxy,
and substituted phenyl-lower alkoxy, or X and Y, or Y and Z, when they are carried by 2 adjacent carbon atoms, together form: —O—(CH₂)ᵣ—O— (in which r is 1 or 2), —O—(CH₂)2— or —O—CH=CH—;

the term "substituted" describing the groups "phenyl" phenyl-lower alkyl" and "phenyl-lower alkoxy" meaning that those groups may be substituted in the phenyl nucleus by one or more substituents selected from halogen, hydroxy, trifluoromethyl, lower alkyl, and lower alkoxy, the terms "lower alkyl" and "lower alkoxy" meaning saturated linear or branched groups containing 1 to 6 carbon atoms inclusive, the terms "lower alkenyl" and "lower alkynyl" meaning unsaturated linear or branched groups containing 2 to 6 carbon atoms inclusive, the term "cycloalkyl" meaning a saturated hydrocarbon ring containing 3 to 8 inclusive, carbon atom in the ring, its possible optical isomers, isolated or in the form of a mixture, and its addition salts with an acid.

8. A pharmaceutical composition useful in the treatment of myocardial ischemic states comprising, as an active ingredient, an effective anti-ischemic amount of at least one compound of claim 1 in combination with one or more pharmaceutically-acceptable excipients or carriers.

9. A method for treating a living animal body afflicted with a condition selected from a clinical manifestation of myocardial ischaemia resulting from an imbalance between the supply and demand of myocardial oxygen, pathology involving rhythm disorders, and atherosclerotic lesions, comprising the step of administering to the said body an amount of a compound of claim 1 which is effective for the alleviation of the said condition.

* * * * *

UNITED STATES PATENT AND TRADEMARK OFFICE
CERTIFICATE OF CORRECTION

PATENT NO. : 5,296,482

DATED : March 22, 1994

INVENTOR(S) : Jean-Louis Peglion, Joel Vian, Jean-Paul Vilaine, Nicole Villeneuve, Philip Janiak, and Jean-Pierre Bidouard It is certified that error appears in the above-indentified patent and that said Letters Patent is hereby corrected as shown below:

Title page, ABSTRACT [57], line 5; insert -- ( -- between "{N-[" and "4,5".

Col. 1, approximately lines 12-18, Formula (I): the formula should NOT be hyphenated, but the two (2) dashes should be connected and should read as just one (1) hyphen in the middle of the formula.

Col. 3, line 24; "g" should read -- q --.

Col. 3, approximately lines 32-38, Formula (I): the formula should NOT be hyphenated, but the two (2) dashes should be connected and should read as just one (1) hyphen in the middle of the formula.

Col. 3, line 42; "M" should read -- m --.

Col. 4, line 10; "3" should read -- ß --.

Col. 4, line 49; "dragdes," should read -- dragées, --.

Col. 5, line 4; "amino)propyl)" should read -- amino}propyl} --.

Col. 5, line 26; "methyl)-" should read -- methyl]- --.

Col. 6, line 9; "amino)propyl)" should read -- amino}propyl} --

Col. 6, line 34; "amino)propyl)" should read -- amino}propyl} --

Col. 6, line 56; insert a comma between "ppm" and "doublet" and between "triplet" and "2H".

Col. 6, line 58; insert a comma between "ppm" and "multiplet,".

Col. 6, line 63; "amino)propyl)" should read -- amino}propyl} --

Col. 7, line 31; "amino)propyl)" should read -- amino}propyl} --

Col. 7, line 43; "amino)propyl)" should read -- amino}propyl} --

Col. 7, line 49; change the semicolon at the end of the line to a colon.

Col. 7, line 65; "N-methyl-" should read -- N-(methyl)- --.

Col. 7, line 66; delete the ")" at the beginning of the line.

Col. 8, line 2; "55%)." should read -- 66%). --.

Col. 8, line 18; "propyl56" should read -- propyl} --.

Col. 8, line 30; "((I)-" should read -- ((1)- --.

Col. 8, line 31; insert a colon after "concentration".

Col. 8, line 48; "amino)propyl)" should read -- amino}propyl} --

UNITED STATES PATENT AND TRADEMARK OFFICE
CERTIFICATE OF CORRECTION

PATENT NO. : 5,296,482

DATED : March 22, 1994

Page 2 of 4

INVENTOR(S) : Jean-Louis Peglion, Joel Vian, Jean-Paul Vilaine, Nicole Villeneuve, Philip Janiak, and Jean-Pierre Bidouard It is certified that error appears in the above-indentified patent and that said Letters Patent is hereby corrected as shown below:

Col. 8, line 58; "85%" should read -- 0.85% --.
Col. 9, line 3; insert "(" before "methyl)".
Col. 9, line 32, at the end of the line; change "methyl-" to -- methyl]- --.
Col. 9, line 33; ")amine" should read -- amine --.
Col. 9, line 36; "N-([4" should read -- N-{[4 -- and "methyl)-" should read -- methyl}- --.
Col. 9, line 53; "methyl)" should read -- methyl] --.
Col. 10, line 29; "ethyl)" should read -- ethyl] --.
Col. 10, line 37; "azino)propyl)" should read -- amino}propyl} --.
Col. 10, line 45; "R,S" should read -- (R,S) --.
Col. 10, line 51, at the end of the line; change "ethyl-" to -- ethyl] --.
Col. 10, line 52; ")amine" should read -- amine --.
Col. 10, line 65; "ethyl)" should read -- ethyl] --.
Col. 11, line 11; "methoxybenzoey-" should read -- methoxybenzocy- --.
Col. 11, line 13; "ons" should read -- one --.
Col. 11, line 16; "benzoey-" should read -- benzocy- --.
Col. 11, line 20; delete the hyphen before "cyclobut".
Col. 11, line 25; ")methyl)" should read -- )methyl] --.
Col. 11, line 42; "3-(3" should read -- 3-{3 --.
Col. 11, line 43; change "amino}propyl}" to -- aminopropyl} --.
Col. 11, line 47; "3-(3" should read -- 3-{3 --.
Col. 11, line 48; change "amino}propyl}" to -- aminopropyl} --.
Col. 11, line 60; ")methyl)" should read -- )methyl] --.
Col. 11, line 65; "0.5 $cm^3$" should read -- 50.5 $cm^3$ --.
Col. 12, line 1; "cm" should read -- $cm^3$ --.
Col. 12, line 60; "Stage A" should read -- Stage $A_3$ --.
Col. 13, line 6; "iodopropyl)" should read -- iodopropyl] --.
Col. 13, line 21; insert a comma between "ppm" and "triplet,".
Col. 13, line 22; insert a comma between "multiplet" and "2H".

UNITED STATES PATENT AND TRADEMARK OFFICE
CERTIFICATE OF CORRECTION

PATENT NO. : 5,296,482

DATED : March 22, 1994

INVENTOR(S) : Jean-Louis Peglion, Joel Vian, Jean-Paul Vilaine, Nicole Villeneuve, Philip Janiak, and Jean-Pierre Bidouard It is certified that error appears in the above-indentified patent and that said Letters Patent is hereby corrected as shown below:

Col. 13, line 33; in both instances, insert a comma between "ppm" and "multiplet".
Col. 13, line 41; "propyl56" should read -- propyl} --.
Col. 14, line 4; delete the hyphen after "benz".
Col. 14, line 15; "[(4--" should read -- [(4- --.
Col. 14, line 16; delete the hyphen at the beginning of line.
Col. 14, line 28; "methyl)-N-(methyl-" should read -- methyl]-N-(methyl)- --.
Col. 14, line 29; ")amine" should read -- amine --.
Col. 14, line 35; "methyl)-N-(methyl-" should read -- methyl]-N-(methyl)- --.
Col. 14, line 36; ")amino" should read -- amine --.
Col. 15, line 16; "ethyl)" should read -- ethyl] --.
Col. 15, line 32; "amino)propyl)" should read -- amino}propyl} --.
Col. 15, line 58; "thyl)" should read -- thyl] --.
Col. 15, line 60; "iodopropyl)" should read -- iodopropyl] --.
Col. 15, line 64; "N-(methyl-" should read -- N-(methyl)- --.
Col. 15, line 65; ")amino)-propyl)" should read -- amino}propyl} --.
Col. 16, line 9; "azino)propyl)" should read -- amino}propyl} --.
Col. 16, line 36; "[2,3-b)" should read -- [2,3-b] --.
Col. 16, line 59; "3-(3" should read -- 3-{3 --.
Col. 16, line 60; "propyl)" should read -- propyl} --.
Col. 17, line 24; "cardia" should read -- cardiac --.
Col. 18, approximately lines 28-34, Formula (I): the formula should NOT be hyphenated, but the two (2) dashes should be connected and should read as just one (1) hyphen in the middle of the formula.
Col. 18, line 42; "2" should read -- q --.
Col. 19, line 12; insert -- form -- after "together".
Col. 19, line 24; insert a colon after "form".

UNITED STATES PATENT AND TRADEMARK OFFICE
CERTIFICATE OF CORRECTION

PATENT NO. : 5,296,482
DATED : March 22, 1994
INVENTOR(S) : Jean-Louis Peglion, Joel Vian, Jean-Paul Vilaine, Nicole Villeneuve, Philip Janiak, and Jean-Pierre Bidouard It is certified that error appears in the above-indentified patent and that said Letters Patent is hereby corrected as shown below:

Col. 19, line 28; ""phenyl" phenyl-" should read -- "phenyl", "phenyl- --.
Col. 19, line 49; insert a hyphen between "pharmaceutically" and "acceptable".
Col. 19, line 63; "3-(3-(N" should read -- 3-{3-{N --.
Col. 19, line 64; "amino)" should read -- amino} --.
Col. 20, line 20; "2" should read -- q --.
Col. 20, line 51; after "inclusive," insert -- all members except the nitrogen being carbon --.
Col. 20, lines 52 and 53; delete "all members except the nitrogen being carbon".
Col. 20, line 63; "(CH$_2$)2" should read -- (CH$_2$)$_2$ --.
Col. 20, line 66; ""phenyl" phenyl-" should read -- "phenyl", "phenyl- --.
Col. 21, line 10; delete the comma after "inclusive".
Col. 21, line 11; change "atom" to -- atoms --.
Col. 21, line 15; delete "an" at the end of the line.

Signed and Sealed this

Sixth Day of December, 1994

Attest:

BRUCE LEHMAN

Attesting Officer    Commissioner of Patents and Trademarks